US006246918B1

(12) United States Patent
Wang et al.

(10) Patent No.: US 6,246,918 B1
(45) Date of Patent: Jun. 12, 2001

(54) SYSTEM AND METHOD FOR GENERATING DIE SWELL/DRAW DOWN INFORMATION FOR PROFILE EXTRUSION DIE DESIGN

(75) Inventors: Hsin-Pang Wang, Rexford, NY (US); Gopal Rameshchandra Saraiya; Erich Otto Teutsch, both of Pittsfield, MA (US); Thomas Paul Dunton, New Lebanon, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/151,245

(22) Filed: Sep. 14, 1998

(51) Int. Cl.$^7$ ..................................... G06F 19/00
(52) U.S. Cl. ........................ 700/97; 700/196; 700/197; 264/40.1; 264/45.3; 264/45.5; 264/45.9; 428/326; 72/271; 73/54.28; 73/54.35
(58) Field of Search .................. 700/97, 196, 197; 525/239, 199, 166, 179, 197; 264/69, 70, 442, 456, 40.1, 45.3, 45.5, 45.9, 108, 126, 176.1, 323, 461; 73/54.28, 54.35; 428/326; 72/271

(56) References Cited

U.S. PATENT DOCUMENTS

| 3,378,507 | * | 4/1968 | Sargent et al. ................... 521/64 |
| 3,862,265 | * | 1/1975 | Steinkamp et al. ............... 525/285 |
| 4,001,172 | * | 1/1977 | Steinkemp et al. ............... 524/285 |
| 4,229,970 | | 10/1980 | Barker et al. ..................... 73/54.11 |
| 4,449,395 | * | 5/1984 | Kurtz et al. ....................... 73/54.11 |
| 5,109,029 | * | 4/1992 | Malone ............................. 521/79 |
| 5,474,722 | * | 12/1995 | Woodhams ...................... 264/45.3 |
| 5,608,637 | | 3/1997 | Wang et al. ....................... 700/95 |
| 5,926,393 | * | 7/1999 | Wang et al. ...................... 700/197 |
| 6,004,489 | * | 12/1999 | Huang et al. ..................... 264/40.1 |
| 6,153,131 | * | 11/2000 | Huang et al. ..................... 264/40.1 |

FOREIGN PATENT DOCUMENTS

| 0483619A2 | 10/1991 | (EP) . |
| 0748681A | 5/1996 | (EP) . |
| 0748681A1 | 5/1996 | (EP) . |
| 0835735A1 | 10/1997 | (EP) . |

OTHER PUBLICATIONS

Chan et al., Integration of Computing Techniques for Plastics Extrusion Die Design, IEEE., Apr. 1990, pp. 37–42.*

"A New Design Procedure for Profile Extrusion Dies" by P. Hurez, et al, Polymer Engineering and Science, Mid–March 1996, vol. 36, No. 5, pp. 626–635.

"Computer–Aided Design of Extrusion Dies" by M. Jia, et al., Comput. & Graphics, vol. 12, Nos. 3/4, pp. 335–340, 1998.

"Computer Program Slashes Die Design Times" Technology News, Plastics World, Oct. 1995, pp. 12–13.

B. Miller, "Computer Program Slashes Die Design Times", Plastic World, No. 10, Oct. 1995, pp. 12–13.

* cited by examiner

*Primary Examiner*—William A. Cuchlinski, Jr.
*Assistant Examiner*—McDieunel Marc
(74) *Attorney, Agent, or Firm*—David C. Goldman; Jill M. Breedlove

(57) ABSTRACT

A system and a method for generating die swell/draw down information for a profile extrusion die design. A rheometer having a slit die and a puller mechanism coupled thereto provide the die swell/draw down information of a polymer resin material in two dimensions—in the thickness direction and in the width direction. A processor uses the die swell/draw down information to generate a die design chart that contains representations of shear rate, draw rates, and thickness. A designer uses the die design charts to design a profile extrusion die.

23 Claims, 5 Drawing Sheets

SYSTEM AND METHOD FOR GENERATING DIE SWELL/DRAW DOWN INFORMATION FOR PROFILE EXTRUSION DIE DESIGN

BACKGROUND OF THE INVENTION

This invention relates generally to a profile extrusion die and more particularly to a system and method for providing die swell or draw down (hereinafter die swell/draw down) information for designing a profile extrusion die.

Typically, a die designer uses experienced-based rules to derive a profile extrusion die design. After deriving the profile extrusion die design, the designer implements the design in an extrusion process. The designer then evaluates the design to determine if the die land length, die opening thickness, and die opening width produce the desired profile dimensions. If the dimensions do not have the desired profile dimensions, then the die is re-cut and implemented in another extrusion process. Usually there is many iterations of cutting and then changing the die before deriving a die design that yields the desired profile dimensions. This design methodology requires a lot of work and time and a tremendous amount of experience-based data. In addition, the designer must modify the die every time the dimensions change or when the extrusion process uses a new plastic resin. These situations also involve more time, work and money. As a result, the designer is reluctant to work with new plastic resins, which hinders the introduction of these resins into the profile extrusion market.

U.S. Pat. No. 5,608,637 discloses a semi-empirical die design methodology that enables a designer to readily design a die that shapes products having varying dimensions and products made from different types of resins. In U.S. Pat. No. 5,608,637, a designer uses a viscoelastic computer software package to provide a representation of a product made from a resin material and shaped by a die. The representation illustrates a relationship between die swell of the resin, shear rate of the resin through the die, and the ratio of die land length of the die to die opening thickness of the die. The designer uses the representation to determine instances where the ratio of die land length to die opening thickness minimizes die swell of the resin. The designer then studies the flow rate effect on die swell for experimental dies in an extrusion process and obtains experimental data therefrom. U.S. Pat. No. 5,608,637 arranges the representation and the experimental data into die design charts and the designer uses the charts to determine profile dimensions of a desired profile extrusion die.

A drawback with U.S. Pat. No. 5,608,637 is that the methodology provided in this patent uses an extruder to develop the die design charts for a particular resin. Using an extruder to develop die design charts is expensive and time consuming. Typically, the extruder needs about two to three gaylords of resin to generate a sufficient number of data points. In addition, the extruder has a tendency to introduce errors at different locations. For example, shear rate measurements and melt temperature control at the extruder die are questionable. The errors produced by the extruder result in the die design charts having inaccurate die swell/draw down values. Therefore, there is a need for a methodology that can provide die swell/draw down information for profile extrusion die design that is simpler, faster, and more accurate than the information provided by an extruder.

BRIEF SUMMARY OF THE INVENTION

In a first embodiment of this invention, there is disclosed a system for generating die swell/draw down information of a polymer resin material. The system comprises a rheometer comprising a barrel for receiving the polymer resin material and a piston for packing the resin material in the barrel as a function of a shear rate setting. A slit die, coupled to the rheometer, generates an extrudate as the piston packs the polymer resin material. A puller mechanism coupled to the slit die, pulls the extrudate at a plurality of draw rates. A processor determines the die swell/draw down information from thickness measurements obtained from samples of the extrudate at each of the plurality of draw rates and the shear rate.

In a second embodiment of this invention, there is disclosed a method for obtaining die swell/draw down information of a polymer resin material with a rheometer having a slit die and an puller mechanism coupled thereto. The method comprises specifying a shear rate setting for operating the rheometer. After specifying the shear rate setting, the next act is filling the polymer resin material into a barrel of the rheometer. After filling the polymer resin material into the barrel, the next act is packing the polymer resin material in the barrel with a piston moving as a function of the shear rate setting. The next act is using the slit die to generate an extrudate as the piston packs the polymer resin material in the barrel. After generating an extrudate, the next act is pulling the extrudate at a plurality of draw rates with the puller mechanism. The next act is collecting a sample of the extrudate at each of the plurality of draw down rates. After collecting a sample of the extrudate, the next act is measuring the thickness for each sample of the extrudate obtained at each of the plurality of draw down rates. The next act is determining the die swell/draw down of each sample of the extrudate as function of the thickness measurements, the plurality of draw rates, and shear rate.

DETAILED DESCRIPTION OF THE INVENTION

The primary objective of this invention is to provide a method for generating die swell/draw down information of a polymer resin material for designing a profile extrusion die. In this invention, the polymer resin may be linear and branched polymers of polycarbonates, polyesters, polyphenylene ethers, polyimides, olefins, polyetherimides, polyamides, polyarylene sulfides, polysulfones, polyetherketones, acrylonitrile butadiene styrene copolymers, polystyrenes and blends, and compositions or copolymers prepared therefrom. In addition, this invention may use other polymers materials such as glass or wood filled polymers. All of these polymer materials exhibit viscoelastic properties and experience die swell/draw down in both the thickness and width direction of the profile. A more detailed discussion on die swell/draw down is provided in commonly assigned U.S. Pat. No. 5,608,637, and U.S. patent application Ser. No. 08/729,997; both of which are incorporated herein by reference.

Figure 1:
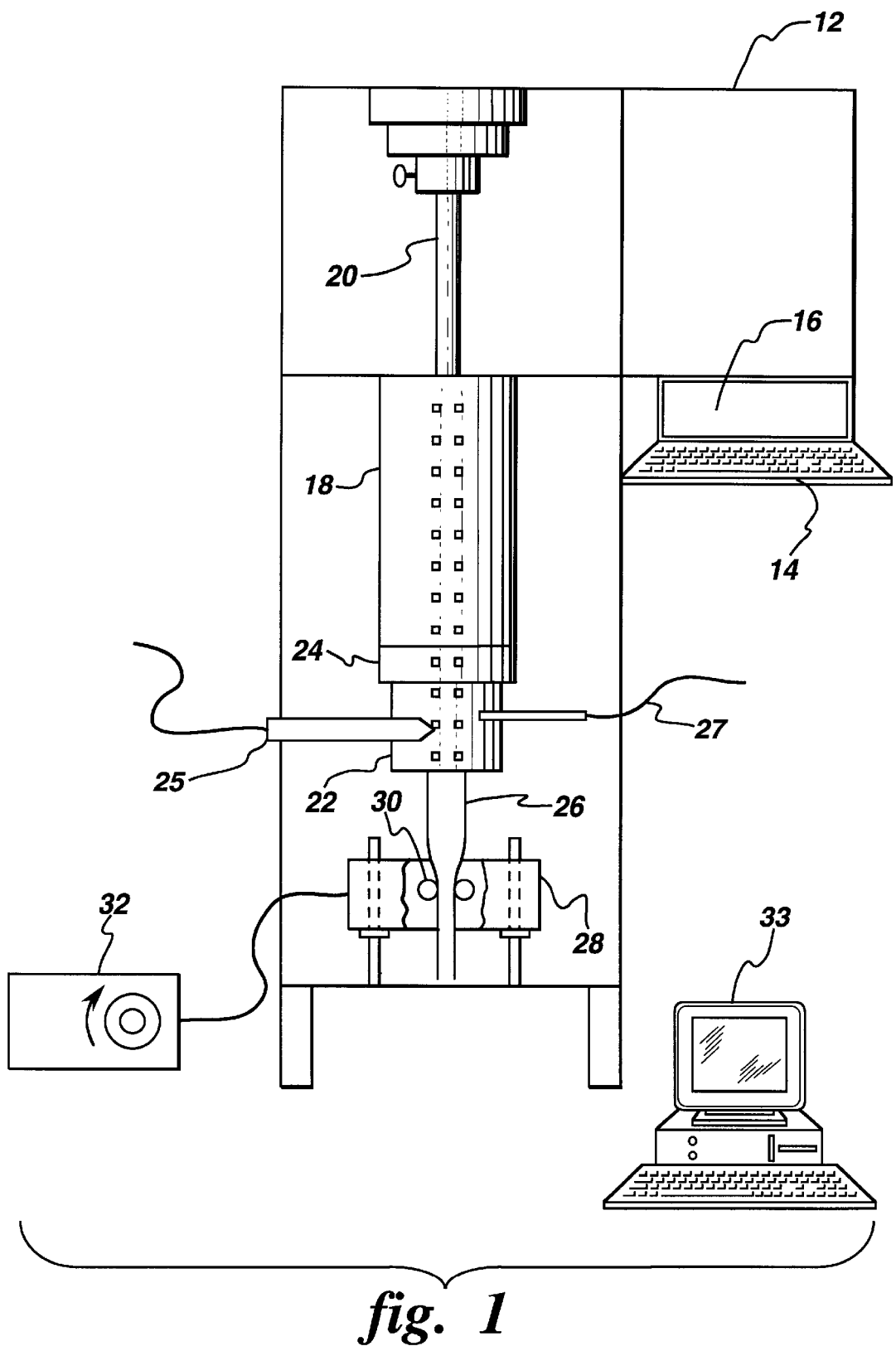
FIG. 1 is a schematic diagram of a system for generating die swell/draw down information of a polymer resin material according to this invention.

FIG. 1 shows a schematic diagram of a system 10 for obtaining die swell/draw down information of a polymer resin material for profile die design according to this invention. The system 10 obtains the information under highly controlled temperature, over a range of shear rate and draw speed. The system 10 comprises a rheometer 12 having an input device such as a keyboard 14 for inputting various operating conditions (e.g., melt temperature and shear rate conditions) and a display 16 for displaying the conditions. The rheometer 12 comprises a barrel 18 which receives the polymer resin material. A hydraulically controlled piston or ram 20 packs the resin material in the barrel 18. The rheometer 12 is a commercially available rheometer such as the Gottfert® rheometer 2001. The system 10 also comprises a slit die 22 coupled to the barrel 18 by an adapter 24, for providing two dimensional flow to simulate a profile geometry. The slit die 22 comprises a first half having a slot extending in a vertical direction and a second half having a flat face. As the piston 20 packs the resin material in the barrel 18, the material passes through the slit die 22 and generates an extrudate 26. A pressure transducer 25 and a melt thermocouple 27, each coupled to the slit die 22, measure the pressure drop across the die and the temperature in the die, respectively.

A puller mechanism 28 pulls the extrudate 26 from the slit die 22 at predetermined draw rate. The puller mechanism 28 comprises two rollers 30; one roller is the "puller" and the other roller is the "idler". Both of the rollers 30 are adjustable in both a horizontal and vertical direction. A roller speed controller 32 controls the speed of the puller mechanism 28. The roller speed controller 32 is preferably a DC motor and is capable of pulling the extrudate 26 at speeds having a range from about 2 ft/min to about 40 ft/min. A pan made of aluminum, steel, or the like collects a sample of the extrudate at each of the plurality of draw rates. Alternatively, the extrudate may also collect on the floor and be cut later with a pair of scissors. The designer retrieves the samples of the extrudate collected at each of the plurality of draw rates and uses a vernier caliper to measure the thickness of each sample. The designer uses a computer processor 33 such as a personal computer or a workstation to determine the die swell/draw down information from the thickness measurements, the plurality of draw rates, and shear rate. Another possible alternative is to use one or two more sets of rollers attached to measuring devices to automatically provide thickness and width data without human intervention and then use the computer to determine die swell/draw down. It is also possible to use the puller roller to obtain thickness data and to calculate width and then use the computer to determine die swell/draw down.

Figure 2:
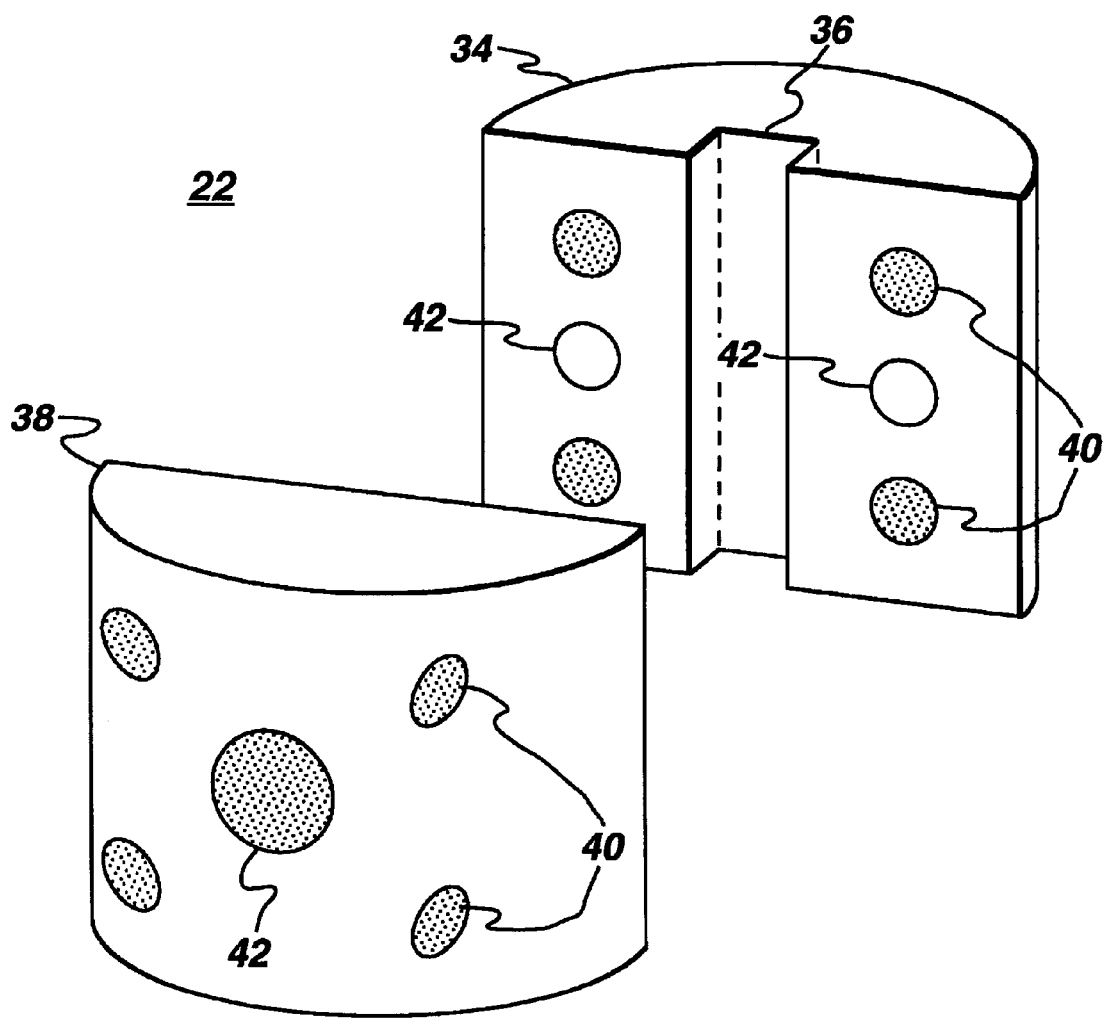
FIG. 2 shows a perspective view of the slit die shown in FIG. 1 with its two halves separated.

FIG. 2 shows a perspective view of the slit die 22 with its two halves separated. In particular, FIG. 2 shows the slit die 22 with a first half 34 having a slot 36 extending in a vertical direction and a second half 38 having a flat face. Preferably, the slot 36 has a thickness that is in the range from about 0.5 mm to about 1.0 mm. A plurality of fasteners 40, such as mounting screws, located at various locations on the first half 34 and the second half 38, connect each half together. In addition, both the first half 34 and the second half 38 have at least one pressure transducer contact 42 embedded therein for measuring pressure drop within the slit die 22. Preferably, slit die 22 has a length of about 100 mm when connecting both the first half 34 and the second half 38.

Figure 3:
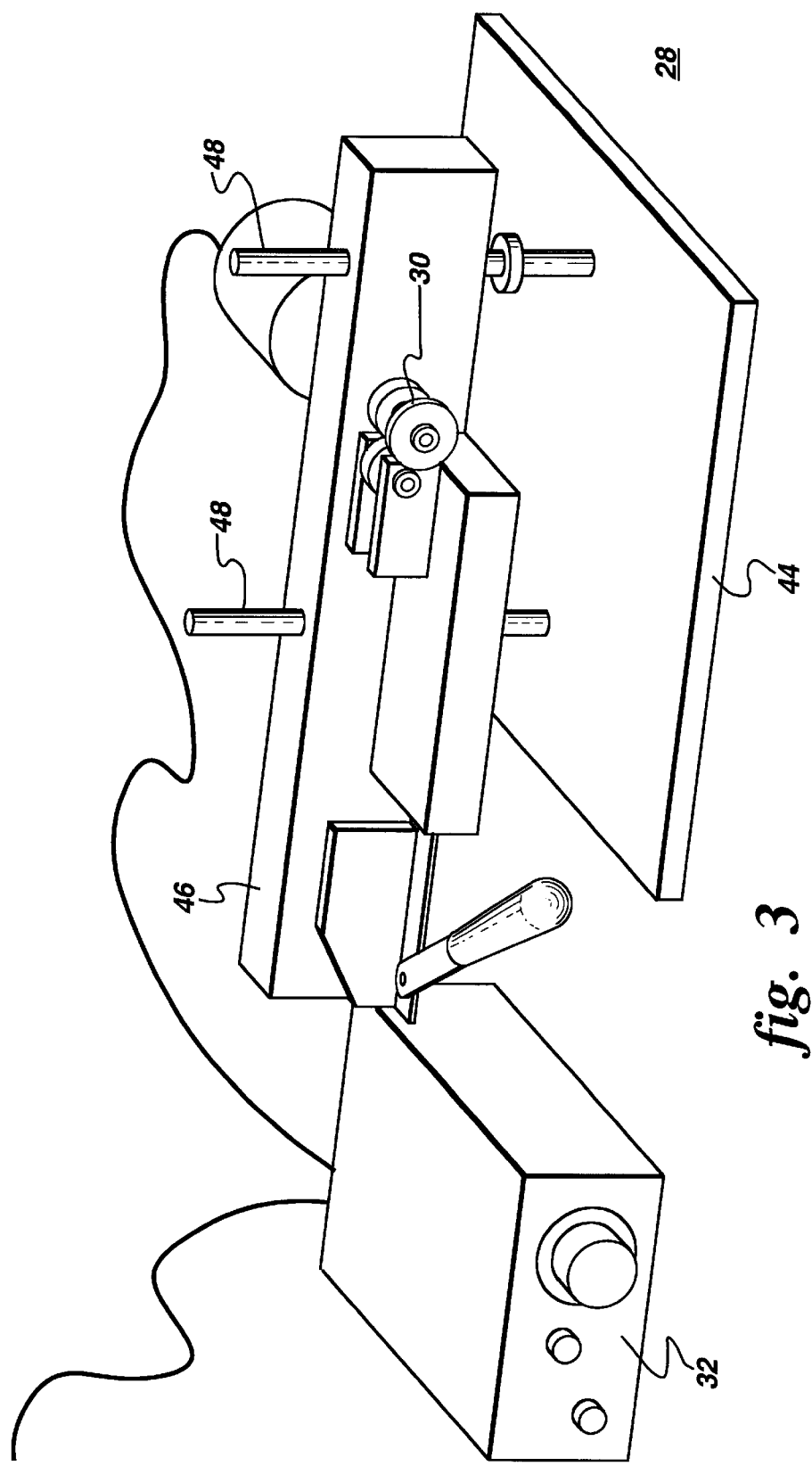
FIG. 3 shows a more detailed view of the puller mechanism shown in FIG. 1.

FIG. 3 shows a more detailed view of the puller mechanism 28 and the roller speed controller 32. In particular, FIG. 3 shows that the puller mechanism 28 comprises a bottom portion 44, a top portion 46 and two supporting poles 48 coupling the bottom portion to the top portion. The bottom portion 44 is preferably a stand made of metal, but other materials such as aluminum may be used. The top portion 46 comprises the two rollers 30; both of the rollers are of low durometer silicon rubber and are adjustable in both the horizontal and vertical direction. One roller is a "puller" roller and the other roller is the "idler" roller. The puller roller attaches to the roller speed controller 32, which controls the speed of the puller. The idler roller attaches with a push-in mechanism that moves the idler in the horizontal direction against the puller roller.

Figure 4:
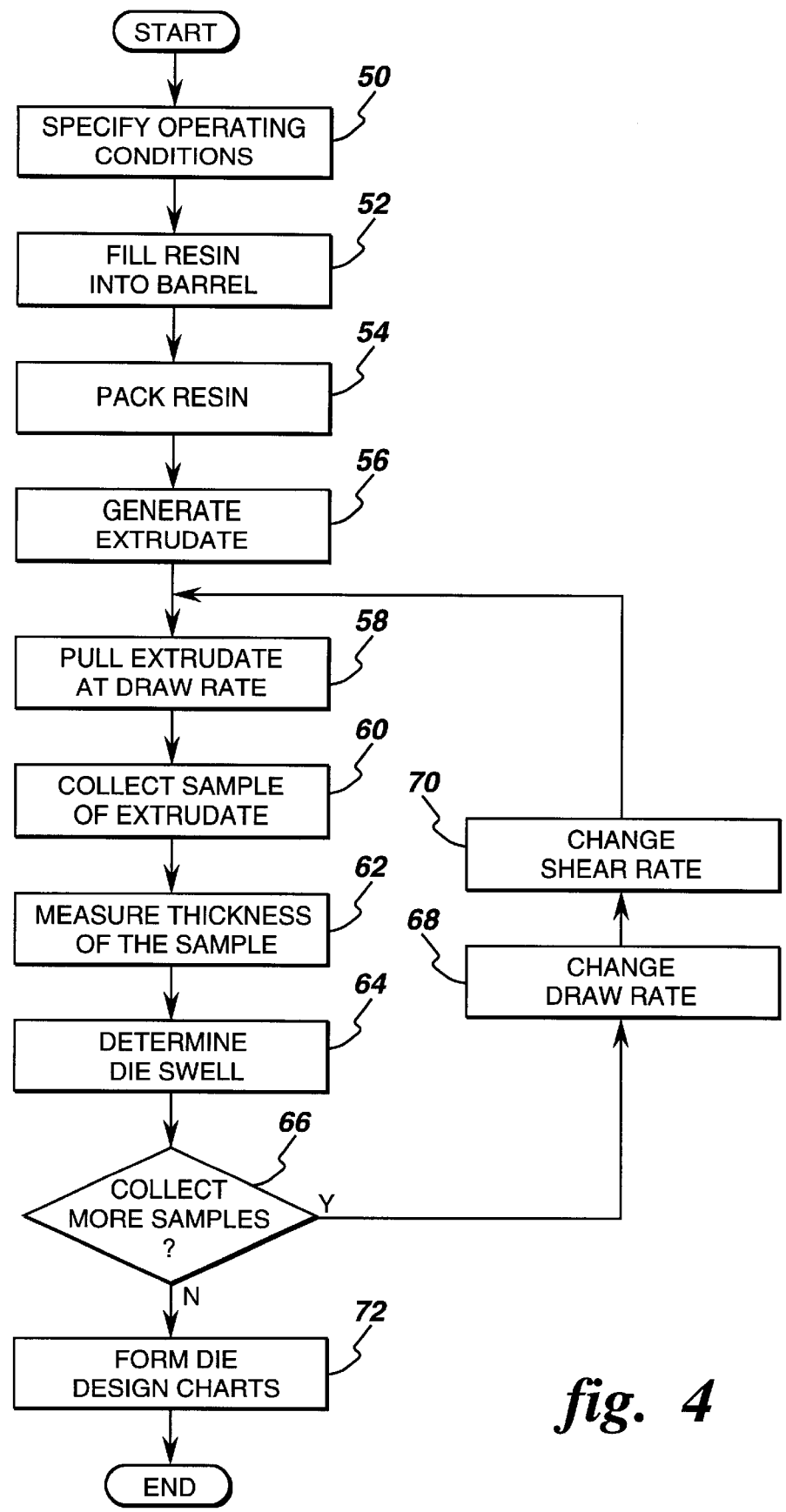
FIG. 4 is a flow chart describing the steps of using the system shown in FIG. 1 to obtain die swell/draw down information for a polymer resin material according to this invention.

FIG. 4 is a flow chart describing the steps of using the system 10 for obtaining die swell/draw down information of a polymer resin material according to this invention. Initially, the designer turns on the rheometer, the barrel heating and the die. Then the designer inputs the operating conditions at 50. In particular, the designer specifies the required melt temperature and shear rate setting. Once the rheometer 12 is at the required melt temperature, then the rheometer is ready to obtain die swell/draw down information. At 52, the designer fills the polymer resin material into the barrel 18 entrapping a minimum amount of air. The piston 20 increases the pressure on the polymer resin material in the barrel 18. Preferably, the piston 20 packs the polymer resin material until the pressure transducer 25 is in the range of about 30–40 bars. The polymer resin material is then preheated for a predetermined time, preferably about 5 minutes. As soon as the preheat time ends, the piston 20 packs the polymer resin in the barrel 18 as a function of the specified shear rate setting at 54. The slit die 22 generates the extrudate 26 at 56 as the piston 20 packs the polymer resin. The initial extrudate coming out of the die is the "zero draw" extrudate.

Figure 5:
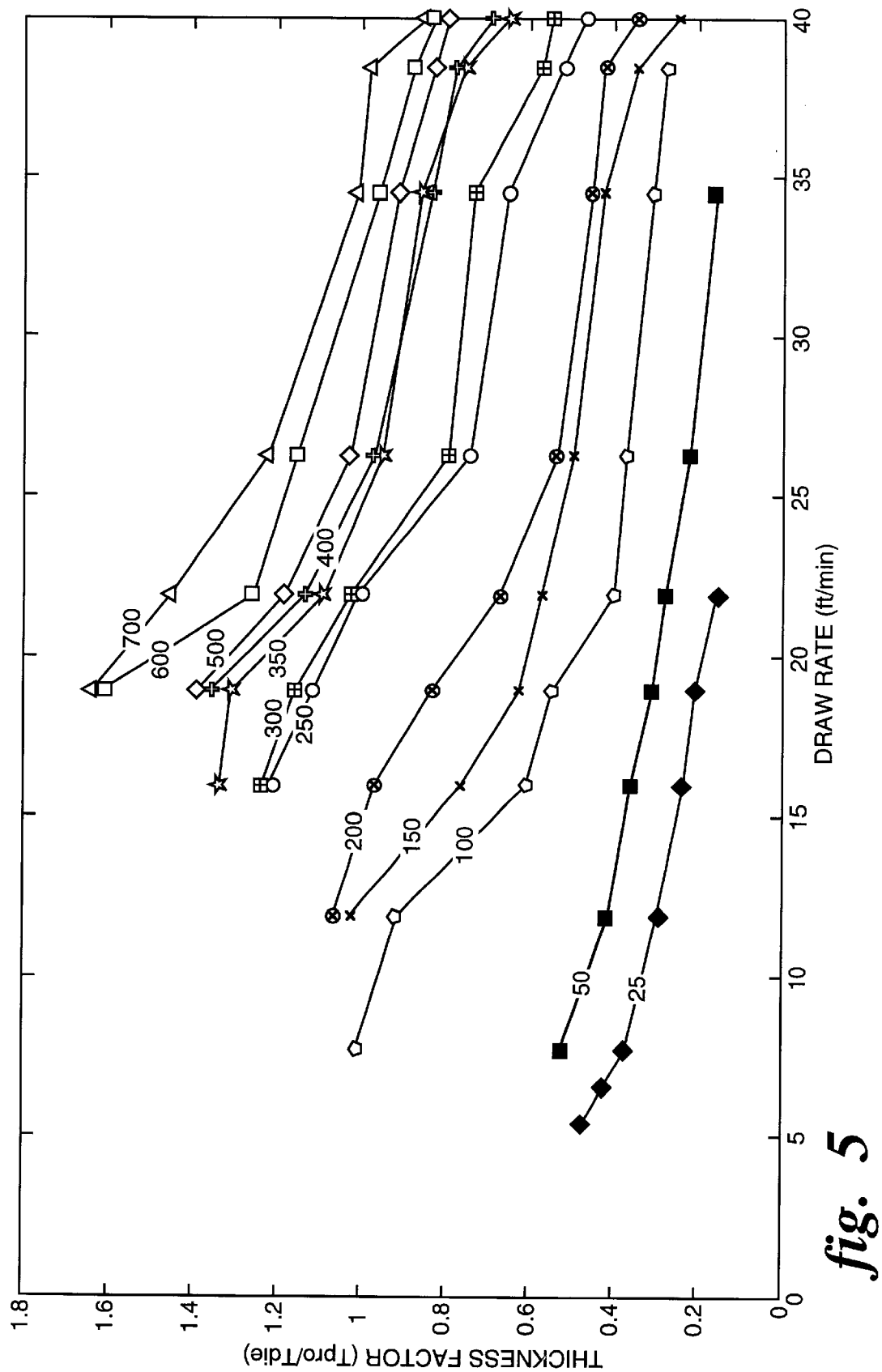
FIG. 5 shows an example of a die design chart generated according to the steps described in FIG. 4.

After taking the "zero draw" sample, the puller mechanism 28 pulls the extrudate at a predetermined draw rate at 58. Prior to contacting the rollers, an air ring can cool the extrudate below its Tg (i.e., glass transition temperature) in order to minimize deformation due to the roll pressure. A sample of the extrudate at the draw rate is collected at 60. The designer then measures the thickness of the sample at 62. Next, the designer uses the processor to determine the die swell of the sample at 64. The die swell represents the material die swell at that particular shear rate and draw rate. At 66, the designer determines whether another set of samples is necessary. If more samples are necessary, then the designer changes the draw rate at 68, the shear rate at 70 and repeats steps 58–66. After collecting samples at all of the different draw rates and shear rates, then the designer uses the processor to form design charts at 72 for designing the die opening thickness and the die opening width. In this invention, a commercially available spreadsheet software package such as Microsoft® Excel is used to plot the die swell (i.e., measured thickness divided by die thickness) data for each shear rate and draw rate. The design charts comprise representations of thickness, draw rates and shear rate values. FIG. 5 shows an example of a die design chart generated according to this invention. The designer then uses the die design charts to determine the dimensions for a profile extrusion die that will shape a polymer resin material into a profile of a product having a desired geometry.

It is therefore apparent that there has been provided in accordance with this invention, a system and method for generating die swell/draw down information for profile die design that fully satisfy the aims and advantages and objectives hereinbefore set forth. The invention has been described with reference to several embodiments, however, it will be appreciated that variations and modifications can be effected by a person of ordinary skill in the art without departing from the scope of the invention.

What is claimed is:

1. A system for generating die swell/draw down information of a polymer resin material, comprising:
   a rheometer comprising a barrel for receiving the polymer resin material and a piston for packing the resin material in the barrel as a function of a shear rate setting;
   a slit die, coupled to the rheometer, for generating an extrudate as the piston packs the polymer resin material;
   a puller mechanism coupled to the slit die for pulling the extrudate at a plurality of draw rates;
   a processor for determining the die swell/draw down information from thickness measurements obtained from samples of the extrudate at each of the plurality of draw rates and the shear rate.

2. The system according to claim 1, further comprising a pressure transducer coupled to the slit die, for measuring the pressure in the slit die.

3. The system according to claim 1, further comprising a thermocouple coupled to the slit die, for measuring the temperature inside the slit die.

4. The system according to claim 1, wherein the puller mechanism comprises a bottom portion; a top portion comprising a puller roller and an idler roller for receiving the extrudate from the slit die; and a support portion for coupling the bottom portion to the top portion.

5. The system according to claim 4, wherein the puller mechanism further comprises a roller speed controller coupled to the top portion for controlling the speed of the puller roller.

6. The system according to claim 1, wherein the processor comprises means for arranging the die swell/draw down information into die design charts containing representations of shear rate, draw rates, and thickness.

7. The system according to claim 6, wherein the processor comprises means for using the die design charts to design a profile extrusion die.

8. A method for obtaining die swell/draw down information of a polymer resin material with a rheometer having a slit die and a puller mechanism coupled thereto, comprising:
   specifying a shear rate setting for operating the rheometer;
   filling the polymer resin material into a barrel of the rheometer;
   packing the polymer resin material in the barrel with a piston moving as a function of the shear rate setting;
   using the slit die to generate an extrudate as the piston packs the polymer resin material in the barrel;
   pulling the extrudate at a plurality of draw rates with the puller mechanism;
   collecting a sample of the extrudate at each of the plurality of draw rates;
   measuring the thickness for each sample of the extrudate obtained at each of the plurality of draw rates; and
   determining the die swell/draw down of each sample of the extrudate as a function of the thickness measurements, the plurality of draw rates, and the shear rate.

9. The method according to claim 8, further comprising specifying additional shear rate settings for operating the rheometer and repeating the steps of filling, packing, using, pulling, collecting, measuring, determining, and forming for each of the additional shear rate settings.

10. The method according to claim 8, further comprising using a pressure transducer to measure the pressure in the slit die.

11. The method according to claim 8, further comprising preheating the polymer resin material in the barrel for a predetermined amount of time after the filling.

12. The method according to claim 8, wherein the collecting comprises obtaining a zero draw down sample of the extrudate.

13. The method according to claim 8, further comprising arranging the die swell information into die design charts containing representations of shear rate, draw rates, and thickness.

14. The method according to claim 13, further comprising using the die design charts to design a profile extrusion die.

15. A system for generating die swell/draw down information of a polymer resin material, comprising:
   a rheometer comprising a barrel for receiving the polymer resin material and a piston for packing the resin material in the barrel as a function of a shear rate setting;
   a die, coupled to the rheometer, for generating an extrudate as the piston packs the polymer resin material;
   a puller mechanism coupled to the die for pulling the extrudate at a plurality of draw rates;
   a processor for determining the die swell/draw down information from thickness measurements obtained from samples of the extrudate at each of the plurality of draw rates and the shear rate.

16. The system according to claim 15, wherein the die comprises a slit die.

17. The system according to claim 15, wherein the processor comprises means for arranging the die swell/draw down information into die design charts containing representations of shear rate, draw rates, and thickness.

18. The system according to claim 17, wherein the processor comprises means for using the die design charts to design a profile extrusion die.

19. A method for obtaining die swell/draw down information of a polymer resin material with a rheometer having a die and a puller mechanism coupled thereto, comprising:
   specifying a shear rate setting for operating the rheometer;
   filling the polymer resin material into a barrel of the rheometer;
   packing the polymer resin material in the barrel with a piston moving as a function of the shear rate setting;
   using the die to generate an extrudate as the piston packs the polymer resin material in the barrel;
   pulling the extrudate at a plurality of draw rates with the puller mechanism;
   collecting a sample of the extrudate at each of the plurality of draw rates;
   measuring the thickness for each sample of the extrudate obtained at each of the plurality of draw rates; and
   determining the die swell/draw down of each sample of the extrudate as a function of the thickness measurements, the plurality of draw rates, and the shear rate.

20. The method according to claim 19, further comprising specifying additional shear rate settings for operating the rheometer and repeating the steps of filling, packing, using, pulling, collecting, measuring, determining, and forming for each of the additional shear rate settings.

21. The method according to claim 19, wherein the collecting comprises obtaining a zero draw down sample of the extrudate.

22. The method according to claim 19, further comprising arranging the die swell information into die design charts containing representations of shear rate, draw rates, and thickness.

23. The method according to claim 22, further comprising using the die design charts to design a profile extrusion die.

* * * * *